(12) United States Patent
Fortson

(10) Patent No.: US 11,918,205 B2
(45) Date of Patent: Mar. 5, 2024

(54) SELF LOCKING SUTURE AND SELF LOCKING SUTURE MEDIATED CLOSURE DEVICE

(71) Applicant: Abbott Cardiovascular Systems, Inc., Santa Clara, CA (US)

(72) Inventor: Aaron M. Fortson, Fremont, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 114 days.

(21) Appl. No.: 17/858,329

(22) Filed: Jul. 6, 2022

(65) Prior Publication Data

US 2022/0330937 A1 Oct. 20, 2022

Related U.S. Application Data

(63) Continuation of application No. 16/546,095, filed on Aug. 20, 2019, now Pat. No. 11,439,383.

(51) Int. Cl.
*A61B 17/04* (2006.01)

(52) U.S. Cl.
CPC ...... *A61B 17/0482* (2013.01); *A61B 17/0401* (2013.01); *A61B 17/0469* (2013.01); *A61B 2017/0409* (2013.01); *A61B 2017/0474* (2013.01); *A61B 2017/0477* (2013.01); *A61B 17/0485* (2013.01); *A61B 2017/0496* (2013.01)

(58) Field of Classification Search
CPC ............ A61B 17/0482; A61B 17/0401; A61B 17/0469; A61B 2017/0409; A61B 17/0485; A61B 2017/0496; A61B 2017/0477; A61B 2017/0474; A61B 17/06166; A61B 2017/00663; A61B 2017/00672; A61B 2017/06176; A61B 17/0057
See application file for complete search history.

(56) References Cited

U.S. PATENT DOCUMENTS

| | | |
|---|---|---|
| 2,238,563 A | 4/1941 | Jacques |
| 2,416,260 A | 2/1947 | Karle |
| 2,449,235 A | 9/1948 | Krupp |
| 3,766,610 A | 10/1973 | Thorsbakken |
| 3,877,434 A | 4/1975 | Ferguson et al. |
| 4,069,825 A | 1/1978 | Akiyama |
| 4,156,574 A | 5/1979 | Boden |
| 4,705,040 A | 11/1987 | Mueller et al. |
| 4,750,492 A | 6/1988 | Jacobs |

(Continued)

FOREIGN PATENT DOCUMENTS

| | | |
|---|---|---|
| WO | 02/15795 A2 | 2/2002 |
| WO | 2005/027754 A1 | 3/2005 |

OTHER PUBLICATIONS

Beartrap definition; http://en.wktionary.org/wiki/beartrap; 1 pg; accessed Dec. 4, 2014.

(Continued)

*Primary Examiner* — Julian W Woo
(74) *Attorney, Agent, or Firm* — Workman Nydegger; Randy Shen

(57) ABSTRACT

An improvement to devices and methods for suturing tissue in various applications, such as percutaneous closure of arterial and venous puncture sites and the like, providing a self-locking or self-securing suture that does not require manual knot-tying to hold in apposition the tissue of the vessel wall on opposite sides of the puncture.

20 Claims, 13 Drawing Sheets

(56) References Cited

U.S. PATENT DOCUMENTS

| | | |
|---|---|---|
| 4,807,333 A | 2/1989 | Boden |
| 5,269,809 A | 12/1993 | Hayhurst et al. |
| 5,292,332 A | 3/1994 | Lee |
| 5,342,393 A | 8/1994 | Stack |
| 5,364,408 A | 11/1994 | Gordon |
| 5,383,905 A | 1/1995 | Golds et al. |
| 5,391,200 A | 2/1995 | Kenknight et al. |
| 5,417,699 A | 5/1995 | Klein et al. |
| 5,435,044 A | 7/1995 | Ida |
| 5,454,140 A | 10/1995 | Murai |
| 5,462,558 A | 10/1995 | Kolesa et al. |
| 5,478,353 A | 12/1995 | Yoon |
| 5,501,692 A | 3/1996 | Riza |
| 5,507,754 A | 4/1996 | Green et al. |
| 5,520,070 A | 5/1996 | Beugelsdyk et al. |
| 5,520,702 A | 5/1996 | Sauer et al. |
| 5,562,688 A | 10/1996 | Riza |
| 5,562,689 A | 10/1996 | Green et al. |
| 5,569,306 A | 10/1996 | Thal |
| 5,572,770 A | 11/1996 | Boden |
| 5,575,800 A | 11/1996 | Gordon |
| 5,584,861 A | 12/1996 | Swain et al. |
| 5,613,974 A | 3/1997 | Andreas et al. |
| 5,630,824 A | 5/1997 | Hart |
| 5,645,553 A | 7/1997 | Kolesa et al. |
| 5,658,313 A | 8/1997 | Thal |
| 5,662,664 A | 9/1997 | Gordon et al. |
| 5,700,272 A | 12/1997 | Gordon et al. |
| 5,702,397 A | 12/1997 | Goble et al. |
| 5,725,529 A | 3/1998 | Nicholson et al. |
| 5,725,556 A | 3/1998 | Moser et al. |
| 5,779,707 A | 7/1998 | Bertholet et al. |
| 5,868,762 A | 2/1999 | Cragg et al. |
| 5,893,856 A | 4/1999 | Jacob et al. |
| 5,899,921 A | 5/1999 | Caspari et al. |
| 5,902,311 A | 5/1999 | Andreas et al. |
| 5,941,901 A | 8/1999 | Egan |
| 6,066,160 A | 5/2000 | Colvin et al. |
| 6,086,608 A | 7/2000 | Ek et al. |
| 6,099,547 A | 8/2000 | Gellman et al. |
| 6,136,010 A | 10/2000 | Modesitt et al. |
| 6,136,017 A | 10/2000 | Craver et al. |
| 6,190,414 B1 | 2/2001 | Young et al. |
| 6,200,329 B1 | 3/2001 | Fung et al. |
| 6,203,554 B1 | 3/2001 | Roberts |
| 6,206,895 B1 | 3/2001 | Levinson |
| 6,228,096 B1 | 5/2001 | Marchand |
| 6,231,592 B1 | 5/2001 | Bonutti et al. |
| 6,245,080 B1 | 6/2001 | Levinson |
| 6,277,140 B2 | 8/2001 | Ginn et al. |
| 6,290,575 B1 | 9/2001 | Shipp |
| 6,398,796 B2 | 6/2002 | Levinson |
| 6,475,230 B1 | 11/2002 | Bonutti et al. |
| 6,712,837 B2 | 3/2004 | Aakerfeldt et al. |
| 6,746,457 B2 | 6/2004 | Dana et al. |
| 6,786,915 B2 | 9/2004 | Akerfeldt et al. |
| 7,011,400 B2 | 3/2006 | Nakano |
| 7,033,370 B2 | 4/2006 | Gordon et al. |
| 7,056,331 B2 | 6/2006 | Kaplan et al. |
| 7,060,077 B2 | 6/2006 | Gordon et al. |
| 7,147,646 B2 | 12/2006 | Dana et al. |
| 7,320,693 B2 | 1/2008 | Pollak et al. |
| 7,361,183 B2 | 4/2008 | Ginn |
| 7,390,328 B2 | 6/2008 | Modesitt |
| 7,435,251 B2 | 10/2008 | Green |
| 7,582,105 B2 | 9/2009 | Kolster |
| 7,662,161 B2 | 2/2010 | Briganti et al. |
| 7,713,284 B2 | 5/2010 | Crofford |
| 7,837,696 B2 * | 11/2010 | Modesitt ............ A61B 17/0057 |
| | | 606/139 |
| 7,842,051 B2 | 11/2010 | Dana et al. |
| 7,875,043 B1 | 1/2011 | Ashby et al. |
| 7,931,670 B2 | 4/2011 | Fiehler et al. |
| 7,947,062 B2 | 5/2011 | Chin et al. |
| 8,048,108 B2 | 11/2011 | Sibbitt et al. |
| 8,100,923 B2 | 1/2012 | Paraschac et al. |
| 8,128,652 B2 | 3/2012 | Paprocki |
| 8,128,653 B2 | 3/2012 | Mcguckin et al. |
| 8,262,736 B2 | 9/2012 | Michelson |
| 8,323,316 B2 | 12/2012 | Maiorino et al. |
| 8,337,522 B2 | 12/2012 | Ditter |
| 8,454,653 B2 | 6/2013 | Hadba et al. |
| 8,480,691 B2 | 7/2013 | Dana et al. |
| 8,579,934 B2 | 11/2013 | Ginn |
| 8,603,137 B2 | 12/2013 | Voss et al. |
| 8,647,364 B2 | 2/2014 | Fiehler et al. |
| 8,685,047 B2 | 4/2014 | Yribarren |
| 8,932,324 B2 | 1/2015 | Sibbitt et al. |
| 8,932,327 B2 | 1/2015 | Kosa et al. |
| 8,945,180 B2 | 2/2015 | Roorda |
| 9,034,011 B2 | 5/2015 | Kirsch et al. |
| 9,055,932 B2 | 6/2015 | Roorda |
| 9,138,214 B2 | 9/2015 | Voss et al. |
| 9,149,265 B2 | 10/2015 | Ehrenreich |
| 9,220,492 B2 | 12/2015 | Cohen et al. |
| 9,241,706 B2 | 1/2016 | Paraschac et al. |
| 9,468,431 B2 | 10/2016 | Ehrenreich |
| 2001/0023352 A1 | 9/2001 | Gordon et al. |
| 2001/0044638 A1 | 11/2001 | Levinson et al. |
| 2001/0044639 A1 | 11/2001 | Levinson |
| 2002/0002401 A1 | 1/2002 | McGuckin et al. |
| 2002/0032454 A1 | 3/2002 | Durgin et al. |
| 2002/0077658 A1 | 6/2002 | Ginn |
| 2002/0082641 A1 | 6/2002 | Ginn et al. |
| 2002/0107542 A1 | 8/2002 | Kanner et al. |
| 2002/0151921 A1 | 10/2002 | Kanner et al. |
| 2002/0169478 A1 | 11/2002 | Schwartz et al. |
| 2002/0188318 A1 | 12/2002 | Carley et al. |
| 2003/0055320 A1 | 3/2003 | McBride et al. |
| 2003/0093096 A1 | 5/2003 | McGuckin et al. |
| 2003/0144695 A1 | 7/2003 | McGuckin et al. |
| 2003/0149447 A1 | 8/2003 | Morency et al. |
| 2003/0167062 A1 | 9/2003 | Gambale et al. |
| 2003/0195514 A1 | 10/2003 | Trieu et al. |
| 2003/0199987 A1 | 10/2003 | Berg et al. |
| 2004/0060410 A1 | 4/2004 | Leung et al. |
| 2004/0093024 A1 | 5/2004 | Lousararian et al. |
| 2004/0122451 A1 | 6/2004 | Wood |
| 2004/0158309 A1 | 8/2004 | Wachter et al. |
| 2005/0038500 A1 | 2/2005 | Boylan et al. |
| 2005/0085853 A1 | 4/2005 | Forsberg et al. |
| 2005/0096697 A1 | 5/2005 | Forsberg et al. |
| 2005/0205640 A1 | 9/2005 | Milliman |
| 2005/0267531 A1 | 12/2005 | Ruff et al. |
| 2006/0004261 A1 | 1/2006 | Douglas |
| 2006/0190037 A1 | 8/2006 | Ginn et al. |
| 2006/0235505 A1 | 10/2006 | Oepen et al. |
| 2006/0241579 A1 | 10/2006 | Kawaura et al. |
| 2006/0265008 A1 | 11/2006 | Maruyama et al. |
| 2006/0265010 A1 | 11/2006 | Paraschac et al. |
| 2007/0010853 A1 | 1/2007 | Ginn et al. |
| 2007/0060895 A1 | 3/2007 | Sibbitt et al. |
| 2007/0149987 A1 | 6/2007 | Wellman et al. |
| 2007/0255317 A1 | 11/2007 | Fanton et al. |
| 2007/0260125 A1 | 11/2007 | Strauss et al. |
| 2007/0270904 A1 | 11/2007 | Ginn |
| 2007/0276433 A1 | 11/2007 | Huss |
| 2007/0276488 A1 | 11/2007 | Wachter et al. |
| 2008/0065156 A1 | 3/2008 | Hauser et al. |
| 2008/0114395 A1 | 5/2008 | Mathisen et al. |
| 2008/0312740 A1 | 12/2008 | Wachter et al. |
| 2009/0012537 A1 | 1/2009 | Green |
| 2009/0069847 A1 | 3/2009 | Hashiba et al. |
| 2009/0157102 A1 | 6/2009 | Reynolds et al. |
| 2009/0306671 A1 | 12/2009 | Mccormack et al. |
| 2009/0306685 A1 | 12/2009 | Fill |
| 2010/0042144 A1 | 2/2010 | Bennett |
| 2010/0179589 A1 | 7/2010 | Roorda et al. |
| 2010/0179590 A1 | 7/2010 | Fortson et al. |
| 2010/0256670 A1 | 10/2010 | Ginn et al. |
| 2011/0029012 A1 | 2/2011 | Tegels |
| 2013/0046331 A1 | 2/2013 | Christensen et al. |
| 2013/0103077 A1 | 4/2013 | Ditter |
| 2013/0110165 A1 | 5/2013 | Burkhart et al. |

(56) References Cited

U.S. PATENT DOCUMENTS

| | | |
|---|---|---|
| 2013/0218206 A1 | 8/2013 | Gadlage |
| 2013/0296887 A1 | 11/2013 | Dana et al. |
| 2013/0345745 A1 | 12/2013 | Kim |
| 2014/0148824 A1 | 5/2014 | Fujisaki et al. |
| 2014/0228868 A1 | 8/2014 | Hassan et al. |
| 2014/0336702 A1 | 11/2014 | Rowe et al. |
| 2014/0364904 A1 | 12/2014 | Kim |
| 2016/0106402 A1 | 4/2016 | Voss et al. |
| 2016/0220235 A1 | 8/2016 | Almedhychy |
| 2017/0135686 A1 | 5/2017 | Ehrenreich |

OTHER PUBLICATIONS

Notice of Allowance received for U.S. Appl. No. 10/941,693, dated Sep. 28, 2011.
Notice of Allowance received for U.S. Appl. No. 12/917,195, dated Aug. 7, 2013.
Notice of Allowance received for U.S. Appl. No. 13/022,246, dated Nov. 14, 2013.
Notice of Allowance received for U.S. Appl. No. 13/035,939, dated Jun. 29, 2015.
Notice of Allowance received for U.S. Appl. No. 13/219,004, dated Feb. 17, 2015.
Notice of Allowance received for U.S. Appl. No. 13/356,129, dated Oct. 7, 2015.
Notice of Allowance received for U.S. Appl. No. 13/411,320, dated May 27, 2015.
Notice of Allowance received for U.S. Appl. No. 14/052,658, dated Jul. 20, 2016.
Notice of Allowance received for U.S. Appl. No. 15/295,096, dated Oct. 30, 2017.
Office Action received for U.S. Appl. No. 10/941,693, dated Dec. 31, 2007.
Office Action received for U.S. Appl. No. 10/941,693, dated Jul. 9, 2008.
Office Action received for U.S. Appl. No. 10/941,693, dated Mar. 2, 2009.
Office Action received for U.S. Appl. No. 10/941,693, dated May 7, 2007.
Office Action received for U.S. Appl. No. 10/941,693, dated Nov. 17, 2006.
Office Action received for U.S. Appl. No. 10/941,693, dated Oct. 23, 2009.
Office Action received for U.S. Appl. No. 11/460,863, dated Apr. 13, 2009.
Office Action received for U.S. Appl. No. 11/460,863, dated Feb. 5, 2008.
Office Action received for U.S. Appl. No. 11/460,863, dated Jul. 12, 2007.
Office Action received for U.S. Appl. No. 11/460,863, dated Oct. 10, 2008.
Office Action received for U.S. Appl. No. 12/917,195, dated Aug. 1, 2012.
Office Action received for U.S. Appl. No. 12/917,195, dated May 6, 2013.
Office Action received for U.S. Appl. No. 13/022,246, dated Jun. 7, 2013.
Office Action received for U.S. Appl. No. 13/022,246, dated May 11, 2012.
Office Action received for U.S. Appl. No. 13/022,246, dated Nov. 28, 2012.
Office Action received for U.S. Appl. No. 13/035,939, dated Apr. 10, 2014.
Office Action received for U.S. Appl. No. 13/035,939, dated Aug. 21, 2014.
Office Action received for U.S. Appl. No. 13/035,939, dated Jan. 31, 2013.
Office Action received for U.S. Appl. No. 13/035,939, dated Mar. 13, 2015.
Office Action received for U.S. Appl. No. 13/035,939, dated Sep. 10, 2013.
Office Action received for U.S. Appl. No. 13/219,004, dated Aug. 5, 2014.
Office Action received for U.S. Appl. No. 13/219,004, dated Aug. 9, 2013.
Office Action received for U.S. Appl. No. 13/219,004, dated Feb. 14, 2013.
Office Action received for U.S. Appl. No. 13/356,129, dated Jul. 21, 2015.
Office Action received for U.S. Appl. No. 13/356,129, dated Mar. 18, 2015.
Office Action received for U.S. Appl. No. 13/356,129, dated May 6, 2014.
Office Action received for U.S. Appl. No. 13/356,129, dated Sep. 15, 2014.
Office Action received for U.S. Appl. No. 13/411,320, dated Feb. 3, 2015.
Office Action received for U.S. Appl. No. 14/052,658, dated Apr. 22, 2016.
Office Action received for U.S. Appl. No. 14/052,658, dated Mar. 27, 2015.
Office Action received for U.S. Appl. No. 14/052,658, dated Sep. 4, 2014.
Office Action received for U.S. Appl. No. 14/052,658, dated Sep. 18, 2015.
Office Action received for U.S. Appl. No. 14/860,413, dated May 2, 2017.
Office Action received for U.S. Appl. No. 15/295,096, dated May 5, 2017.
Requirement Restriction received for U.S. Appl. No. 12/917,195, dated Jun. 28, 2012.
Requirement Restriction received for U.S. Appl. No. 13/219,004, dated Dec. 19, 2012.
U.S. Application filed Jan. 8, 2010, by Voss et al., U.S. Appl. No. 12/684,470.

\* cited by examiner

SELF LOCKING SUTURE AND SELF LOCKING SUTURE MEDIATED CLOSURE DEVICE

CROSS-REFERENCE TO RELATED APPLICATIONS

This application is a continuation of U.S. patent application Ser. No. 16/546,095, filed Aug. 20, 2019, the entire contents of which are incorporated by reference herein.

FIELD OF THE INVENTION

The present invention relates generally to devices and methods for suturing tissue in various applications, such as percutaneous closure of arterial and venous puncture sites used for vascular access in connection with diagnostic and interventional vascular procedures.

BACKGROUND

A number of diagnostic and interventional vascular procedures are performed translumenally. Such procedures require vascular access, which is usually established during the well-known Seldinger technique, as described, for example, in William Grossman's "Cardiac Catheterization and Angioplasty," 3rd Ed., Lea and Febiger, Philadelphia, 1986, incorporated herein by reference. Briefly summarized, at an access location a trocar can be advanced through the patient's skin, tissue and through the wall of a vessel, such as the femoral artery, to provide access to the vascular lumen. A guidewire can be introduced through the trocar and navigated through the vasculature to the desired treatment site. With the guidewire in place, the trocar can be removed and an introducer sheath can then be advanced over the guidewire until the distal end of the introducer sheath passing through the tissue tract, through the vascular puncture and into the vessel lumen. With the introducer sheath properly positioned within the lumen, a catheter can then be introduced through the introducer sheath into the vascular system and guided by the guidewire through the vascular system to a target treatment location using established techniques.

When vascular access is no longer required, the introducer sheath can be removed, and a percutaneous suture applying device can be introduced through the tissue tract with a distal end of the device extending through the vascular puncture and positioned within the vessel lumen. One or more needles can then be advanced distally from an intermediate portion of the suture device, passing through the tissue of the vessel wall adjacent to the access puncture site. The one or more needles are then used to draw a suture through the blood vessel wall on opposite sides of the access opening, and the device is withdrawn from the tissue tract, bringing with it the ends of the suture. In such devices, a knot is then manually tied between the suture ends and advanced down the tissue tract until it is positioned against the outer surface of the vessel wall over the adventitial surface of the vessel wall, thereby drawing the tissue on opposite sides of the access opening together and forming a highly reliable closure of the puncture site. Another option is to secure the suture limbs together with a clamp or locking tab that is manually advanced over the individual suture limbs and through the tissue tract, positioned next to the puncture site, and clamped to hold the sutures in place. However, manually forming and manipulating knots and/or positioning a separate clamping member can be difficult, time consuming and, if not done properly, can lead to additional complications, delays and unreliable or insufficient closure of the access opening. It would, therefore, be an improvement to the art to provide a suture-based, percutaneous closure device comprising a self-locking or self-securing suture that does not require or rely on manually tied knots, clamps and/or locking tabs to secure the suture in place at the puncture site.

BRIEF SUMMARY

Various embodiments of a self-locking or self-securing suture are disclosed herein. Also disclosed are various embodiments of a self-locking suture mediated closure device that are particularly suited for closing a puncture formed in a vessel wall, such as the femoral artery, for the purpose of providing vascular access for transluminal diagnostic or treatment purposes. The self-locking suture can include one or more knots positioned in the bight or middle section of the suture. The one or more knots can have a one or more selected sizes, can be spaced at one or more selected intervals, and/or can be located over one or more selected lengths of the suture. The diameter of the knots can be chosen such that they are large enough that they will not readily pass through the needle penetrations formed in the vessel walls without the application of a predetermined amount of force that is sufficient to cause the needle penetrations to elastically deform to a diameter sufficient to allow the knots to pass therethrough. And, once a knot passes through a needle penetration, the elasticity of the vessel wall causes the tissue surrounding the needle penetration to retract to a diameter less than the diameter of the knots, thereby preventing the same or a successive knot from passing through the needle penetration again, in either direction, unless and until sufficient force is once again applied to the suture. Tactile feedback can also be achieved as each knot passes through a needle penetration. Opposing ends of the suture can be withdrawn until opposite sides of the puncture site are drawn together in apposition, with adjacent knots positioned against the needle penetrations located on opposite sides of the vessel puncture. In this position, the elasticity of the vessel wall will prevent the knots from passing back through the needle penetrations, and the suture will be locked in place with the tissue on opposite sides of the puncture site being securely held together in apposition.

DETAILED DESCRIPTION

In the accompanying Figures, "S" will generally indicate the surface of a patient's skin adjacent a vascular access location, "T" will generally indicate tissue located between the skin and the vessel through which vascular access will be rendered, "TT" will generally refer to the tissue tract formed through the tissue by a trocar or other access device, "VW" will generally indicate the vessel wall, "VL" will generally indicate the vessel lumen, "P" will generally indicate the primary puncture made in the vessel wall for the purposes of providing vascular access to the vessel lumen, and "NP" will generally indicate penetrations in the vessel wall made adjacent to the primary puncture by needles of a closure device as described herein.

Figure 1:
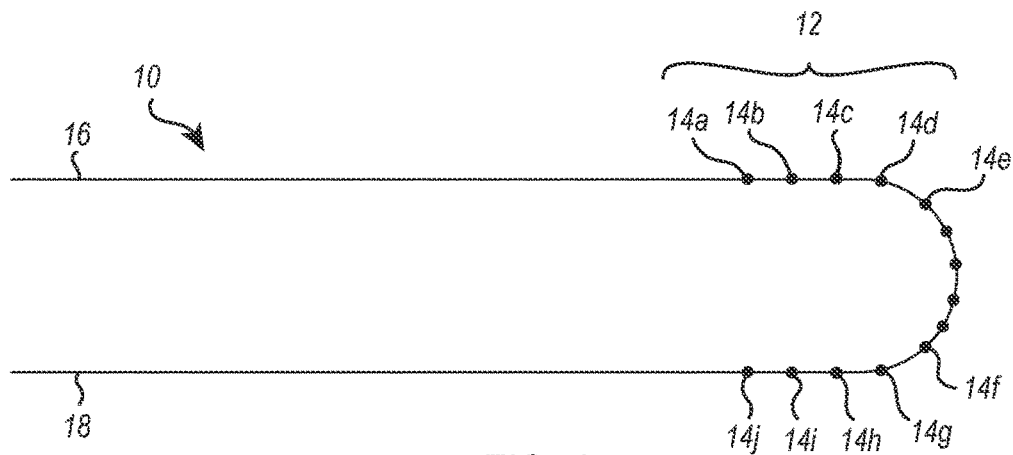
FIG. 1 is a schematic representation of one embodiment of a self-locking or self-securing suture.

Referring now to the drawing, FIG. 1 illustrates one embodiment of an improved, self-locking suture 10 for use in a suture-based, percutaneous vascular closure device. Suture 10 differs from a standard monofilament suture in that the bight or middle section 12 of suture 10 can include one or more knots, such as knots 14a to 14j. Knots 14 can have one or more selected sizes, can be spaced at one or more selected intervals, and can be spread over one or more selected lengths of suture 10 as graphically illustrated in FIG. 1. The spacing of the knots can also be varied to accommodate different thicknesses of the arterial wall. Suture 10 can also include suture limbs 16 and 18 located on either side of bight 12 and, more particularly, can include an anterior suture limb 16 and a posterior suture limb 18. Each of knots 14 can be formed by means of one or more overhand or other suitable knots, as may be necessary, to form a knot having a desired diameter. Knots 14 can all have the same diameter or certain of knots 14 can be larger or smaller in diameter than others of knots 14.

The specific diameter(s) of knots 14 can be selected based on, among other things, the relative diameter of the needles used to pierce the walls of the vessel to be closed, the cross-sectional diameter of suture 14, the degree of elasticity of the vessel walls, etc. Preferably, the diameter of knots 14 should be chosen such that they should be large enough that they will not readily pass through the tissue of the needle penetrations without the application of a predetermined amount of force that is sufficient to cause the needle penetrations to elastically deform to a diameter sufficient to allow the knot 14 to pass therethrough. And, once a knot 14 passes through a needle penetration, the elasticity of the vessel wall causes the tissue surrounding the needle penetration to retract to a diameter less than the diameter of knot 14, thereby preventing the same or a successive knot 14 from passing through the needle penetration again, in either direction, unless and until sufficient force is once again applied to one or both of suture limbs 16 and 18. It will also be appreciated that tactile feedback will be provided to the surgeon as each knot 14 passes (i.e., "snaps") through a needle penetration, which can be tactically sensed by the surgeon through suture limbs 16 and 18.

Figure 2A:
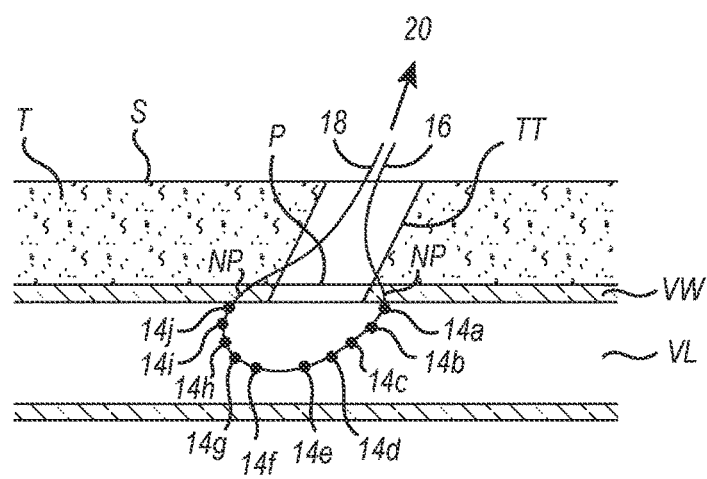
FIGS. 2A and 2B are schematic representations illustrating the self-locking/securing suture embodiment shown in FIG. 1 in different stages of advancement of the suture within a vascular access opening.
Figure 2B:
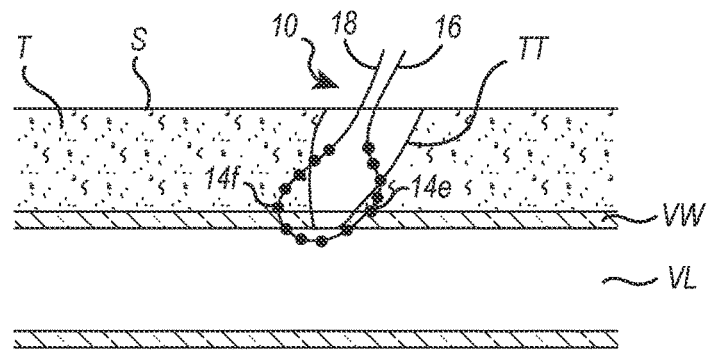

In this embodiment, suture 10 can be delivered into the vessel lumen by a closure device and can be drawn in a proximal direction through the vessel wall and out through the tissue tract, as will be explained below in relation to FIGS. 7-13. Referring to FIG. 2A, suture 10 is drawn through the vessel wall by pulling on both suture limbs 16 and 18 in a proximal direction. In the illustrated example, as an adequate force is applied to the opposing limb ends 16 and 18 in a proximal direction as indicated by arrow 20, the ends of suture limbs 16 and 18 will continue to withdraw from the tissue tract, thereby causing successive knots 14b, 14c, 14d and 14e and successive knots 14i, 14h, 14g and 14f, respectively, to pass through the opposing needle penetrations, and thereby drawing the tissue located on opposite sides of the puncture site together in apposition to one another. And, once all of knots 14 are withdrawn through the needle penetrations, knots 14e and 14f will be positioned against the outer surface of the vessel wall on opposite sides of the puncture site with a short portion of suture bight 12 extending therebetween. In this position, the elasticity of the vessel wall will prevent knots 14e and 14f from passing back through the needle penetrations. Thus, suture 10 will be locked in place with the tissue on opposite sides of the puncture site being drawn together in apposition as graphically illustrated in FIG. 2B. Of course, any other pair of adjacent knots could also be selected to close the puncture site by selectively pulling limbs 16 and 18 to varying degrees so as to position the desired pair of knots adjacent to opposing sides of the puncture site.

Figure 3:
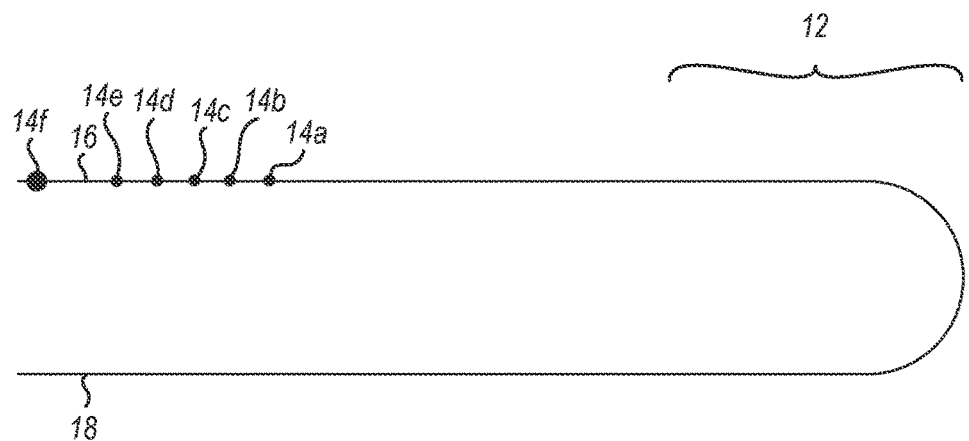
FIG. 3 is a schematic representation of a second embodiment of a self-locking or self-securing suture.
Figure 4A:
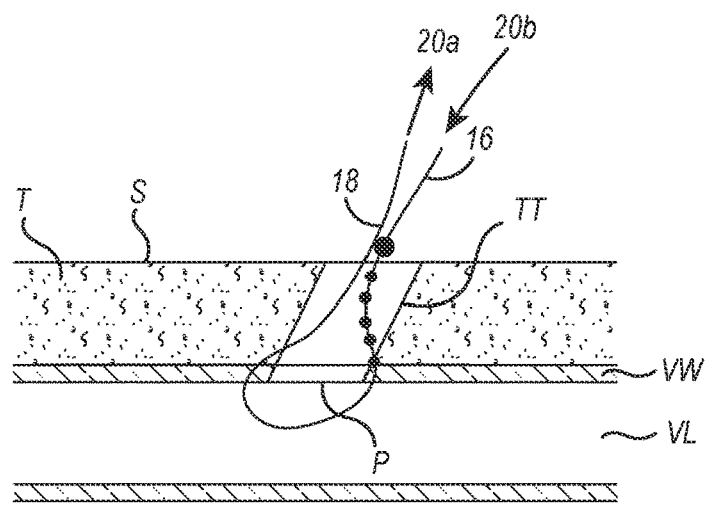
FIGS. 4A and 4B are schematic representations illustrating the self-locking/securing suture embodiment shown in FIG. 3 in different stages of advancement within a vascular access opening.
Figure 4B:
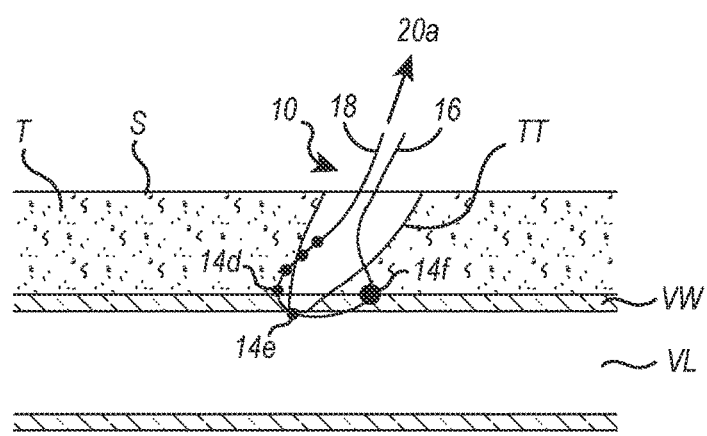

A second embodiment is illustrated in FIGS. 3 and 4. This embodiment is designed to be delivered by a second embodiment of a closure device, as explained below in relation to FIG. 14. In this embodiment, the suture is delivered into the tissue tract by the delivery device and is initially drawn distal in a distal direction through a needle penetration in the vessel wall to one side of the access puncture, passes through a portion of the vessel lumen, and is drawn back out through another needle penetration in the vessel wall located on the opposite side of the access puncture. In this embodiment, suture 10 is positioned by pulling on only one of suture limbs 16 or 18. In this embodiment, suture 10 can include multiple knots 14a to 14e, all of which can have a substantially uniform diameter with properties similar to those described above. In addition, a suture 10 can also have an anchor knot 14f, which is larger in diameter than knots 14a to 14e and which is large enough that it will not be able to pass through the tissue surrounding either needle penetration, even upon the application of the predetermined force that will cause the smaller knots 14a to 14e to pass therethrough.

As suture limb 16 is pulled with sufficient force in a proximal direction as indicated by the arrow, this can cause knots 14a to 14e to initially travel in a distal direction and pass through a needle penetration to one side of the puncture, travel through a portion of the vessel lumen, and then travel in a proximal direction and pass through the other needle penetration on the other side of the puncture. However, due to the enlarged diameter of knot 14f, it will not be able to pass through the anterior needle penetration, but will instead be held against the outer surface of the vessel wall. And, once all of knots 14a to 14e are withdrawn through the posterior needle penetration, knots 14e and 14f will be positioned against the outer surface of the vessel wall on opposite sides of the puncture site with a short portion of bight 12 extending therebetween. Additional knots can also be provided and positioned adjacent the intimal wall as well. In this position, the elasticity of the vessel wall will prevent knots 14e and 14f from passing back through the needle penetrations. Thus, suture 10 will be locked in place with the tissue on opposite sides of the puncture site being drawn together in apposition as graphically illustrated in FIG. 4B. Here, again, any other pair of adjacent knots could also be selected to close the puncture site by selectively pulling limbs 16 and 18 to varying degrees so as to position the desired pair of knots adjacent to opposing sides of the puncture site.

The self-locking/securing sutures 10 disclosed herein may be made of any suitable, bio-compatible suture material. For example, any of the following materials, separately or in combination, could be used to fashion sutures 10: nonabsorbable olypropylene, polyamide and polyester; absorbable polyglactin 10, polycaprolate, poliglecaprone 25, polysorb, polydioxanone, polytrimethylene carbonate, polyglytone 621, etc.

Figure 5A:
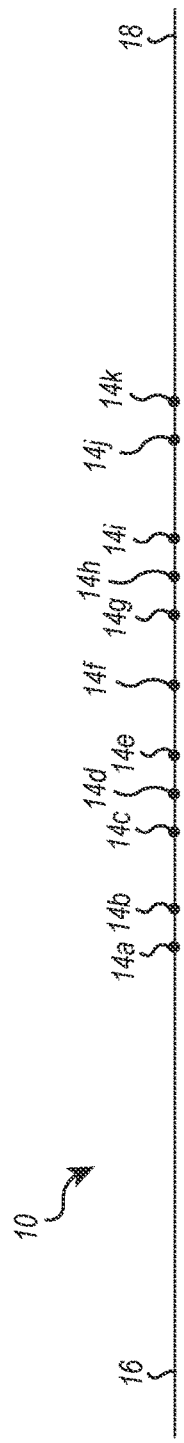
FIG. 5A is a side view illustrating the spacing of one possible embodiment in accordance with the embodiment shown in FIG. 1.
Figure 5C:
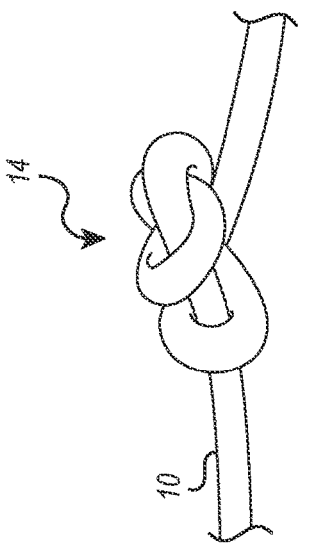
FIG. 5C is a schematic illustration of one example of a double knot structure.
Figure 5D:
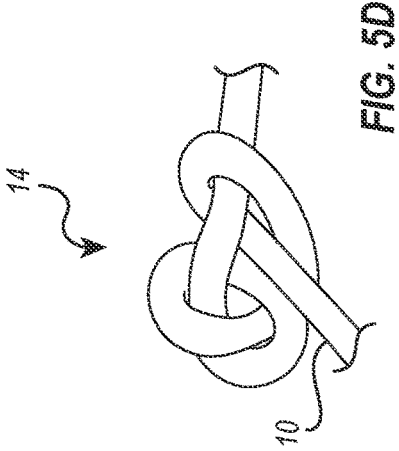
FIG. 5D is a schematic illustration of one example of a triple knot structure.
Figure 5B:
FIG. 5B is a schematic illustration of one example of a single knot structure.

Referring now to FIG. 5A, one representative example of suture 10 is provided, including a representative example of knot diameter and spacing for closing an access puncture in a femoral artery of an adult human patient. For example, human artery thickness can vary from approximately 0.004" (0.10 mm) to approximately 0.093" (2.36 mm) based upon the absence or presence of arterial disease. The number and positioning of knots can take into consideration the full target range of tissue thickness conditions. In the illustrated example, suture 10 can have suture diameter of approximately 0.0098" (0.25 mm) based on a needle diameter of approximately 0.019" (0.48 mm), can have an overall length of approximately 50 cm and is shown to have eleven knots 14a to 14k. For simplicity the knots are schematically represented by a single round dot in the accompany Figures. In the reality the knots can have a generally "pretzel" shape and can have projections that can be characterized by a maximum diameter. The knot can be formed by a simple overhand knot, as schematically illustrated in FIG. 5B, or the overall size can be increased by tying a second simple knot over the first, as schematically illustrated in FIG. 5C, or can be further increased by tying a third knot over the first two, as schematically illustrated in FIG. 5D. Based on aforementioned suture diameter, a single knot diameter can range from approximately 0.011" (0.28 mm) to approximately 0.026" (0.66 mm), a double knot diameter can range from about 0.028" (0.71 mm) to about 0.036" (0.91 mm), and a triple knot diameter can range from about 0.038" (0.97 mm) to about 0.052" (1.32 mm). In the illustrated example, a tension force of between about 2 Newtons and about 6 Newtons may be required, depending on the tissue modulus (i.e., extent of calcification of the vessel wall) to cause knots 14a to 14k to penetrate through a typical needle penetration in the vessel wall. The spacing between knots can be uniform or, as shown in the illustrated example, the knot spacing can be varied. As illustrated, the spacing between knots 14a and 14b, between knots 14c to 14e, between knots 14g to 14i and between knots 14j and 14k can be approximately 0.020" (0.51 mm) each, whereas the spacing between knots 14b and 14c, between knots 14e and 14f, between knots 14g and 14h and between knots 14i and 14j can be approximately 0.039" (0.99 mm) each. In the illustrated example, the knot pattern is symmetrical, but non-symmetrical knot patterns can also be used, such as, for example, in the embodiment illustrated in FIGS. 3 and 4. In the illustrated example, the knot sizes are shown as being uniform, but the knot sizes can vary to suit a particular need or as discussed above in relation to FIGS. 3 and 4.

Figure 6A:
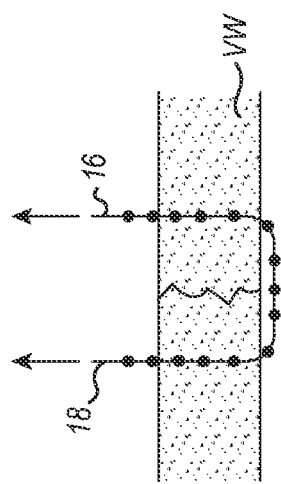
FIGS. 6A-6F illustrate various possible permutations of self-locking/securing suture embodiments that can include one or more of: pre-tied knots positioned on the suture bight as shown in FIGS. 1-5; other physical structures formed of a bio-compatible material and bonded to the suture bight; heat-formed, resilient shape-memory structures formed along at least a portion of the suture bight; and/or additional knots tied in the suture limbs following placement of the other self-locking/securing suture structures.

FIG. 6A illustrates the suture pattern shown in FIG. 5A with suture 10 having been positioned around a vascular access puncture site and drawing the tissue adjacent to the puncture together in apposition. In the illustrated example, a tension force of between about 6 Newtons and about 13 Newtons may be required to effectively close and seal the puncture, depending on the size of knots used and the modulus of the tissue. As also illustrated in FIG. 6A, a plurality of pre-tied intermediate anchors can be distributed through and/or across the vessel tissue to form a tissue engaging surface area. In one embodiment, the tissue engaging surface area formed by the plurality of pre-tied intermediate anchors can be about 0.1" (2.54 mm) to about 0.6" (1.52 cm).

Figure 6B:
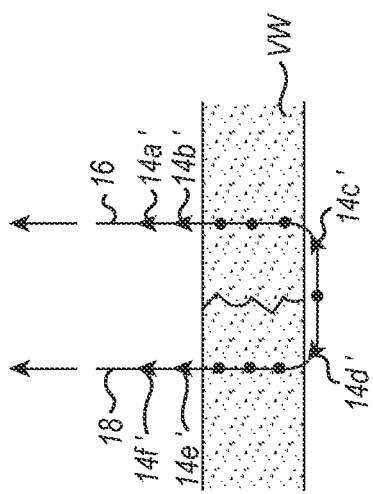

In addition to knots formed in the bight of suture 10, other physical structures can be used to secure suture 10 in place without departing from the inventive concept. For example, instead of knots formed from the suture material itself, bodies of a desired shape and/or size can be molded or otherwise formed out of a suitable bio-compatible material and can be bonded or otherwise securely affixed to suture 10 at the desired location(s). For example, such physical structures could take the form of spheres, cones, cylinders, cubes, etc. As illustrated in FIG. 6B, conical shapes 14' with the small end oriented in the direction of travel of the suture may be of particular interest, since such structure would aid in advancing the structure through tissue and, at the same time, once through the tissue, the enlarged base of the cone would help resist the structure from passing back through the tissue in the opposite direction.

In addition, other surface treatments could also be provided on the bight of the suture itself and/or on the physical structures to assist resisting further movement once the suture has been properly positioned and the force applied to the suture limbs has been removed. For example, a layer of friction enhancing material could be deposited on one or more portions of the suture bight and/or knots 14 or other physical structures 14' to enhance or increase the amount of friction between these structures and the surrounding tissue.

Figure 6C:
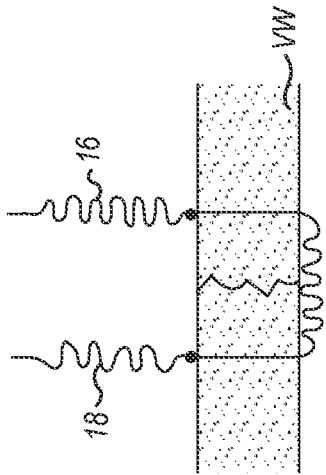

FIG. 6C illustrates another alternative structure that can be used to create a self-locking or self-securing suture. In this embodiment, all or part of suture 10 can be heat-treated to form resilient, shape-memory structures, such as loops or coils 14″, as graphically illustrated in FIG. 6B. Under tension, the thermoformed coils would partially uncoil creating "serrated" or "zig-zag" segments of the suture, which could help resist suture pull through. As with the knots discussed above, the shape-memory structures can be made to have properties that allow individual loops or coils to pass through the needle penetrations upon the application of predetermined force to one or more of the suture limbs, but that will resist further relative movement without a subsequent application of such predetermined force.

Figure 6D:
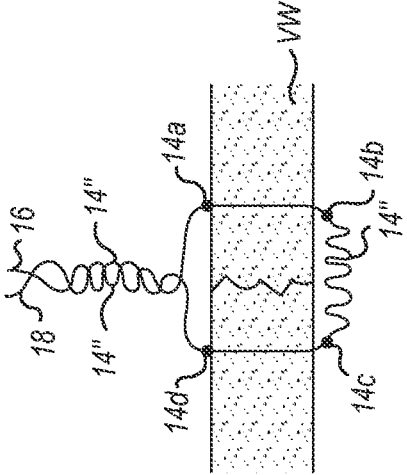
Figure 6E:
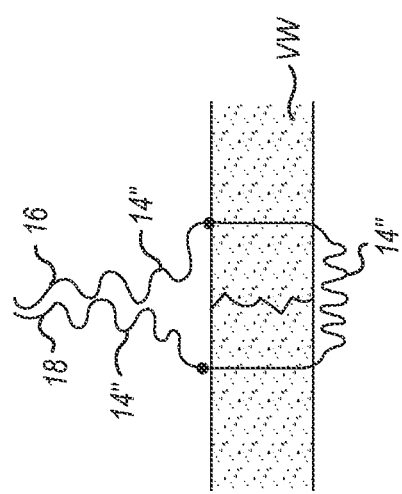
Figure 6F:
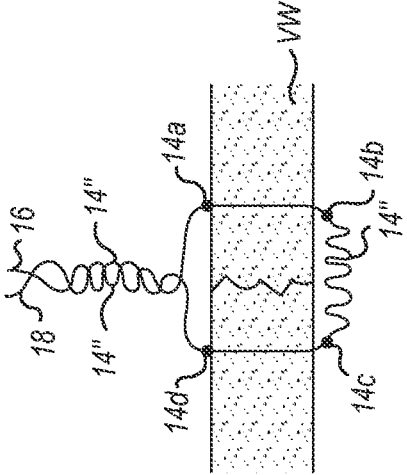

FIGS. 6D to 6F illustrate the concept that the aforementioned features can also be selectively combined (i.e., the use of knots, other shapes bonded to the suture and/or shape-memory structures can be combined in any desired combination) to achieve a self-locking/securing suture having the desired performance characteristics.

Although one of the purposes of providing a self-locking/securing suture as discussed above is to eliminate the need for the attending physician to manually tie a knot in the suture limbs once the suture is properly position, FIGS. 6E and 6F illustrate that the self-locking/securing sutures disclosed here still provide access to the suture limbs so that an attending physician still has the option to further secure the suture by manually tying the suture limbs together.

Figure 7A:
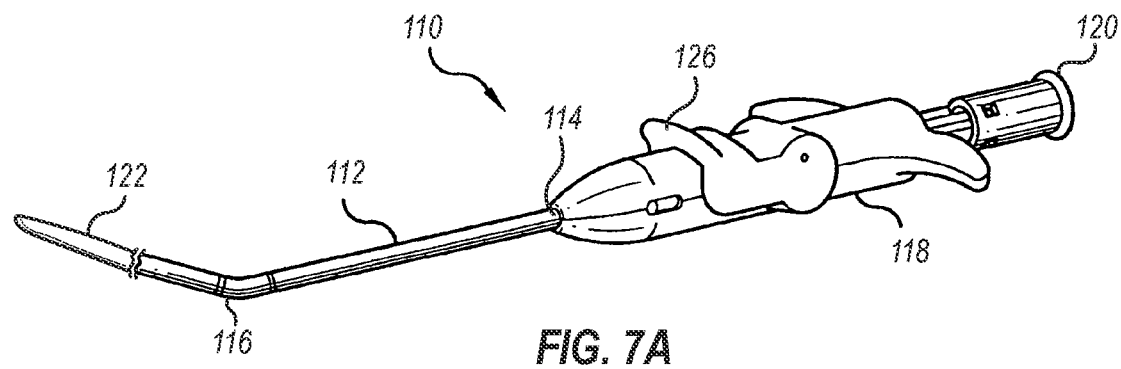
FIGS. 7A-7C are perspective views of one embodiment of a percutaneous blood vessel closure device.
Figure 7B:
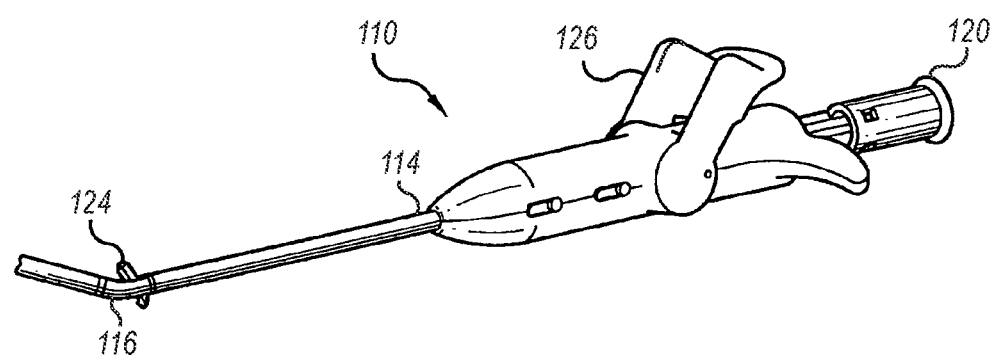
Figure 7C:
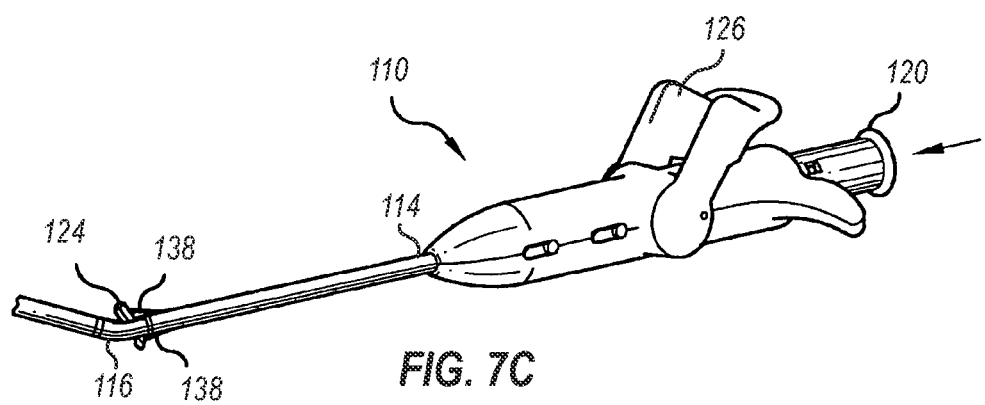

Referring now to FIGS. 7A-7C, a vessel closure device 110 can generally have a shaft 112 having a proximal end 114 and a distal end 116. A proximal housing 118 can support a needle actuation handle 120. A flexible, atraumatic monorail guidebody 122 can extend distally of distal end 116 of shaft 112.

A foot 124 can be articulatably mounted near the distal end of shaft 112. Foot 124 can move between a low profile configuration, in which the foot can be substantially aligned along an axis of shaft 112 (as illustrated in FIG. 7A), to a deployed position, in which the foot extends laterally from the shaft (as illustrated in FIGS. 7B and 7C), upon actuation of a foot actuation handle 126 disposed on proximal housing 118. FIG. 7C also illustrates how needles 138 can be advanced distally from shaft 112 to the foot by depressing needle actuation handle 120.

Figure 8A:
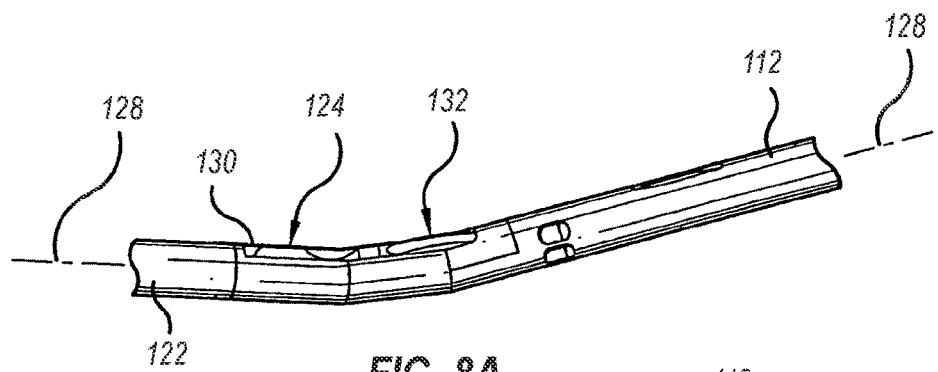
FIGS. 8A and 8B are views showing details of the foot of the vessel closure device of FIG. 7 in a parked position prior to deployment (FIG. 8A) and in a deployed position (FIG. 8B) following deployment.
Figure 8B:
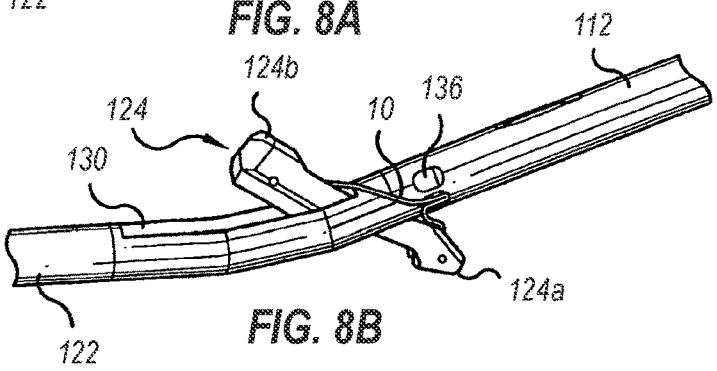

Actuation of foot 124 is illustrated more clearly in FIGS. 8A and 8B. In the parked position illustrated in FIG. 8A, foot 124 can extend substantially along axis 128 of shaft 112. Note that the axis of the shaft need not be straight, as the shaft may curve somewhat, particularly adjacent the foot. In the exemplary embodiment, foot 124 can be substantially disposed within a foot receptacle 130 of shaft 112 so as to minimize the cross-section of the device adjacent the foot prior to deployment. Prior to deployment of the foot, device 110 can have a cross-section adjacent foot 124 of about 7 Fr or less, ideally having a cross-section of about 6 Fr or less for the entire device distally of the proximal end 114 of shaft 112.

The actuation of foot handle 126 can slide a foot actuation wire 132 proximally, pulling foot 124 from a parked position (FIG. 8A) to the deployed position (FIG. 8B). Once deployed, a first end 124a and a second end 124b of foot 124 can extend laterally from the shaft. Suture 10 can comprise a continuous filament, with one or more knots or other anchors formed at an intermediate position as described above, and ends disposed in needle receptacles adjacent each end of the foot.

Shaft 112 can also include a foot position verification lumen that extends distally from a position verification port 136 to a position indicator at housing 118. When the foot is properly positioned within the blood vessel, blood pressure will cause blood to flow proximally through the indicator lumen to the indicator. The indicator may optionally comprise a blood exit port, a clear receptacle in which blood is visible, or the like. In the exemplary embodiment, the indicator of handle 118 can comprise a length of clear tubing extending from housing 118 (not shown) in which the blood is clearly visible. It should be understood that a wide variety of alternative position verifications sensors might be used, including electrical pressure sensors, electrolytic fluid detectors, or the like.

Figure 9A:
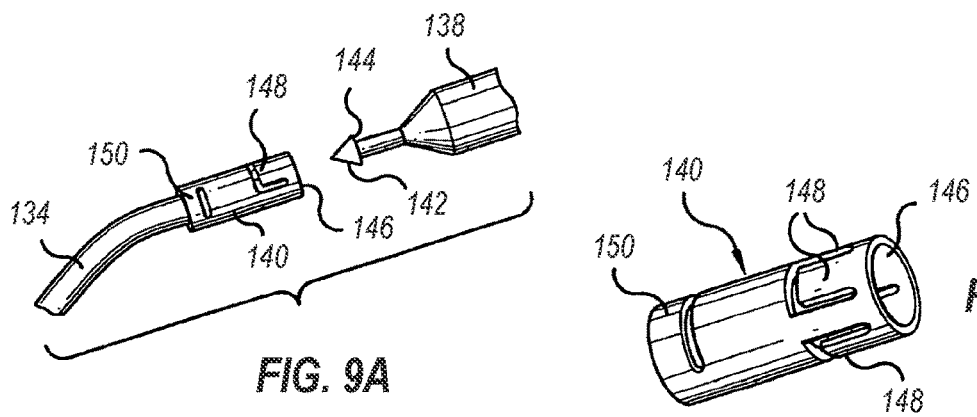
FIGS. 9A and 9B are perspective views illustrating a suture attachment cuff and an associated barbed needle for use in the vessel closure device of FIG. 7.
Figure 9B:
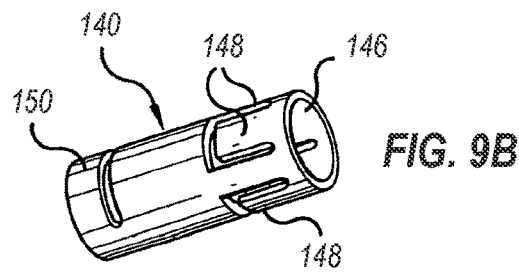
Figure 10:
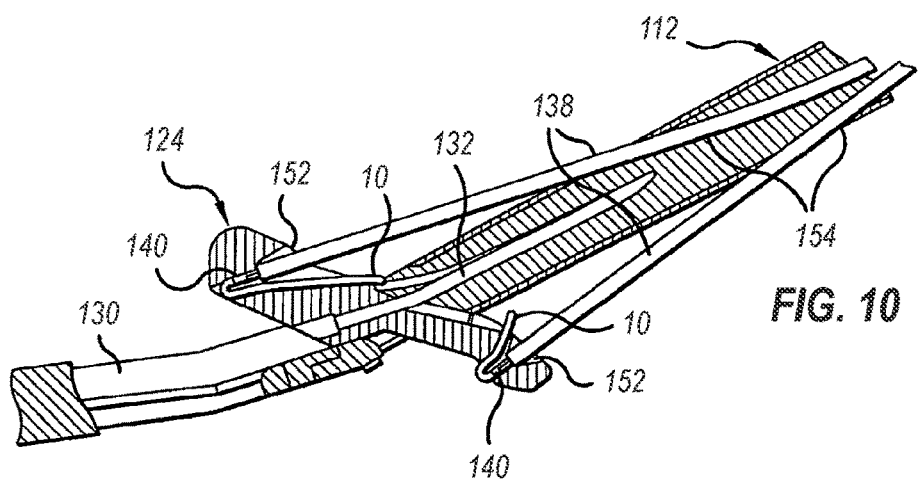
FIG. 10 is a cross-sectional view showing the barbed needles securingly engaging the suture cuffs of the deployed foot.

The structures used in positioning a loop of suture across the puncture can be understood with reference to FIGS. 9A, 9B and 10. In general terms, needles 138 can extend from shaft 112 into secured engagement with fittings 140 attached to sutures 10. More specifically, needles 138 can include a barbed end 142 defining a recessed engagement surface 144. Fittings 140 can be roughly cylindrical structures having an axial channel 146 which receives the barbed end 144 of needle 138 therein. A first slot can be cut in fitting 140 so as to define at least one tab 148. Tabs 148 can be resiliently biased inward into channel 146. As needle 138 advances into fitting 140, barbed end 142 can resiliently displace tab 148 clear of channel 146 so as to allow the barbed end to pass axially into the fitting. Once barbed end 142 is disposed axially beyond tab 148, the tab can resiliently flex back into the channel, capturing needle 138 by engagement between the tab and recessed surface 144. As each tab can hold the fitting in place on the needle, the use of more than one tab can increase the reliability of the system. As illustrated in FIG. 9B, three radially spaced apart tabs 148 can be provided.

To facilitate attachment of fitting 140 to suture 10, a second slot cut in the tubular fitting structure can define a suture attachment collar 150. Optionally, collar 150 may be crimped about suture 10 to mechanically affix the suture to fitting 140. In addition, and/or instead of mechanical crimping, suture 10 may be bonded to fitting 140 using an adhesive, heat, fasteners, knots, mechanical crimping, swaging or the like.

Fitting 140 can be quite small in size, and can be generally configured to facilitate withdrawing the fitting (and the attached suture) along with needle 138 axially through the vessel wall along the needle path. Needle 138 can generally have a cross-sectional width of between about 0.010″ (0.25 mm) and 0.020″ (0.51 mm). Barb 142 can extend laterally so as to define an engagement surface 144 having a protruding length of between about 0.002″ (0.05 mm) and 0.005″ (0.13 mm). Fitting 140 can have a cross-sectional size roughly corresponding to or only slightly larger than needle 138. Fitting 140 can have an outer lateral width of between about 0.014″ (0.36 mm) and 0.025″ (0.64 mm), and an axial length of between about 0.035″ (0.89 mm) and 0.050″ (1.27 mm). Channel 146 can be sized to receive at least a portion of needle 138, and can generally have a width of between about 0.010″ (0.25 mm) and 0.020″ (0.51 mm). Suture 10 can extend axially opposite the open end of channel 146 to minimize drag when the suture is drawn proximally along the needle path. In the exemplary embodiment, needle 138 can have a diameter of about 0.020″ (0.51 mm), while the fitting can comprise a tube having an outer diameter of about 0.020″ (0.51 mm), an inner diameter of about 0.016″ (0.41 mm), and an overall length of about 0.047″ (1.19 mm). The fitting can also comprise a resilient material, preferably comprising a metal, and in the exemplary embodiment, comprising stainless steel.

Needles 138 can have a length of between about 5.0" (12.7 cm) and 6.0" (15.2 cm), and can be sufficiently stiff to be advanced in compression through the vessel wall (and adjacent tissues) for up to 0.5" (1.27 cm) when supported in cantilever. Nonetheless, the needles can be flexible enough to be laterally deflected within shaft 112, as can be understood with reference to FIG. 10. Needles 138 can comprise a high strength metal, ideally comprising stainless steel. Fittings 140 can also comprise a flexible material to allow tab 148 to flex out of the way of barbed end 142, and to resiliently rebound and engage recessed surface 144. In the exemplary embodiment, barbed end 142 can have a diameter of about 0.015" (0.38 mm), with the diameter of the needle decreasing to about 0.008" (0.2 mm) proximally of the barb so as to define the recessed engagement surface.

As was generally described above, foot 124 can include needle receptacles 152 adjacent to the ends of the foot. A fitting 140 (with an associated end of suture 10) can be disposed within each needle receptacle, and a surface of the receptacle can taper proximally and outwardly so as to guide the advancing needles 138 into engagement with fittings 140 when foot 124 is in the deployed position. As fittings 140 (and associated portions of suture 10) are releasable supported in the foot, needles 138 can be withdrawn proximally to draw the fittings and suture ends from the foot proximally into (and optionally through) shaft 112. The needle receptacles of the exemplary embodiment can taper outward at an angle between 20 and 35 degrees from the centerline of fitting 140, and the fitting can be held in a recess having a diameter of about 0.0230 (0.58 mm) and a length of about 0.042" (1.07 mm). A lateral opening or window through the side of foot to the fitting recess may be provided to facilitate needle and/or cuff positioning during assembly of the probe, and a protruding collar near the proximal end of the fitting recess may help keep the fitting in position.

FIG. 10 also illustrates the lateral deflection of needles 138 by needle guides 154 of shaft 112. This lateral deflection of the needles can allow the use of a small diameter shaft, while still encompassing sufficient tissue within the suture loop on opposite sides of the puncture so as to effect hemostasis when the suture looped is tightened and secured. In the exemplary embodiment, shaft 112 can comprise an outer casing of a biocompatible material such as stainless steel, carbon fiber, nylon, another suitable polymer, or the like. Needle guides 154 may be defined at least in part as lumens formed within the casing of a polymeric material such as nylon or the like. In some embodiments, shaft 112 may comprise a carbon fiber filled nylon, or carbon fiber filled with an alternative material.

Figure 11A:
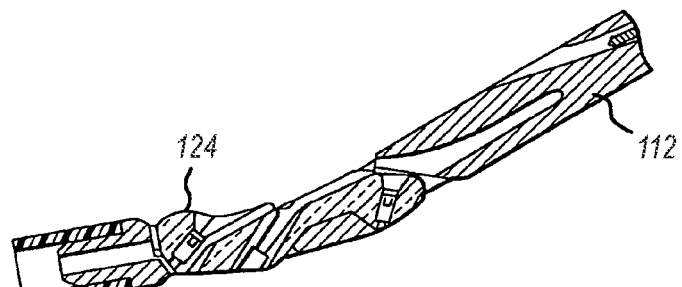
FIGS. 11A-11C illustrate one embodiment of a deployable foot, in which the foot slides and pivots when drawn proximally by a tension member.
Figure 11B:
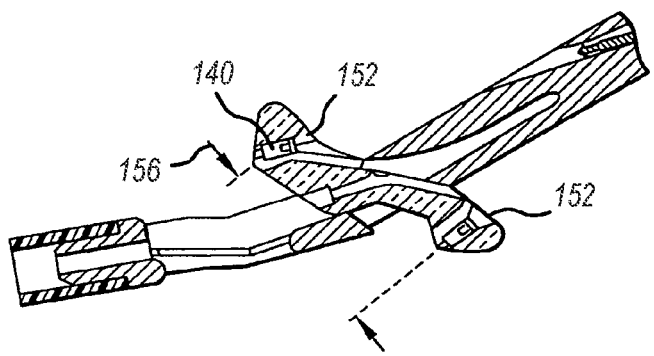
Figure 11C:
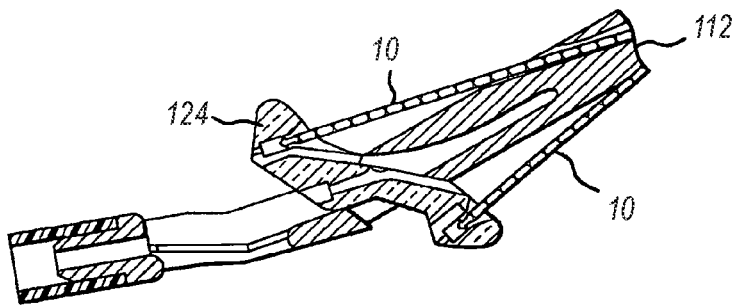

One example of a suitable structure and articulation motion for foot 124 is illustrated in FIGS. 11A and 11B. Foot actuation wire 132 (see FIG. 8A) can ride in a lumen of shaft 112, and draw foot 124 from a parked position (shown in FIG. 11A) to a deployed position (shown in FIG. 11B) through a pivoting motion, a sliding motion or a combination of sliding and pivoting motions of the foot. The foot can remain supported throughout its range of motion by arms disposed laterally on either side of the foot, the arms defining (at least in part) foot receptacle 130. Once foot 124 is deployed, needle receptacles 152 and/or the fittings disposed therein can define a lateral suturing width 156 in a range from about 0.260" (6.6 mm) to about 0.300" (7.62 mm). Foot 124 may be machined or cast from a polymer or metal, but can also comprise a polymer such as carbon fiber filled nylon. In some cases, foot 124 may be molded as two separate halves which can subsequently be affixed together. Needles 138 advance from the fixed needle guides 154, and are laterally directed into fittings 140 by receptacles 152, as illustrated in FIG. 11C. In general, a shape memory alloy such as Nitinol™ in its superelastic regime can provide a particularly advantageous actuator wire for manipulating foot 124.

Figure 12:
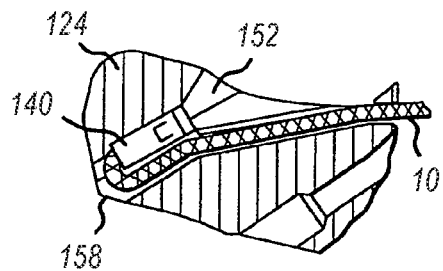
FIG. 12 illustrates the suture cuff positioned within a needle receptacle, and also shows how the suture is releasably secured within a slot extending radially from the needle receptacle.

Referring now to FIG. 12, fittings 140 and suture 10 can be withdrawn proximally by the needles from needle receptacles 152. To releasably support fittings 140 and suture 10 and avoid entanglement of the suture in the needles, suture 10 can be fittingly received within a slot 158 which extends laterally from needle receptacles 152. Slot 158 can be appropriately sized to accept suture 10, including the knots 14 or such other anchor structures as may be formed thereon. As the needles pull the fitting axially from needle receptacles 152, suture 10 can be pulled from slot 158 and free from foot 124. Bending of the suture proximally within the suture slot can also locally increase the suture width, so that the interaction between the bent suture and the slot can help hold the fitting in the recess.

Figure 13A:
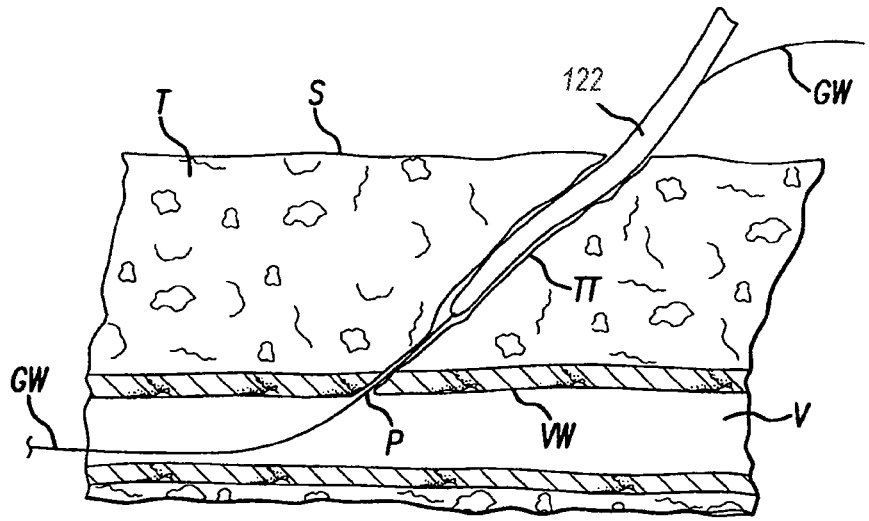
FIGS. 13A-13G illustrate one embodiment of a self-locking suture mediated closure system and method adapted for use with the self-locking/securing suture embodiment shown in FIG. 1.
Figure 13B:
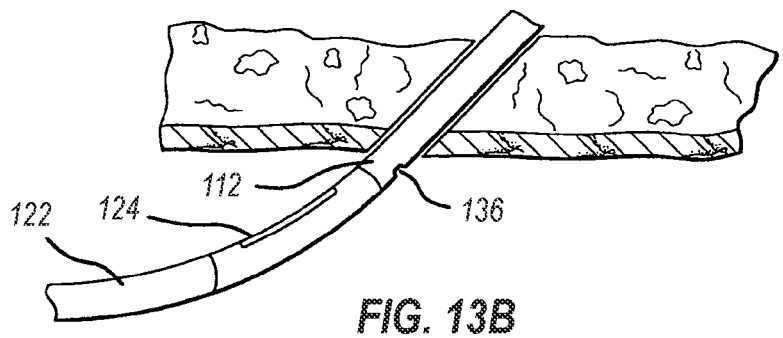

The structure and method of use of the closure device can be further understood with reference to FIGS. 13A-G. After accessing a blood vessel V (often using the Seldinger technique), a guidewire GW can be left extending into skin S and down through tissue T along tissue tract TT. Guidewire GW enters vessel V through a puncture P in vessel wall W, and extends along the vessel throughout many endovascular procedures. As illustrated in FIG. 13A, distal guidebody 122 can be advanced over the guidewire GW in a monorail fashion, so that the guidewire helps to direct the probe along the tissue tract TT and into the vessel through puncture P. FIG. 13B shows that when sensor 136 is disposed within the vessel, blood can flow from the sensor port and through a lumen in shaft 112 to the proximal handle to notify the operator that foot 124 has been advanced far enough for deployment.

Figure 13C:
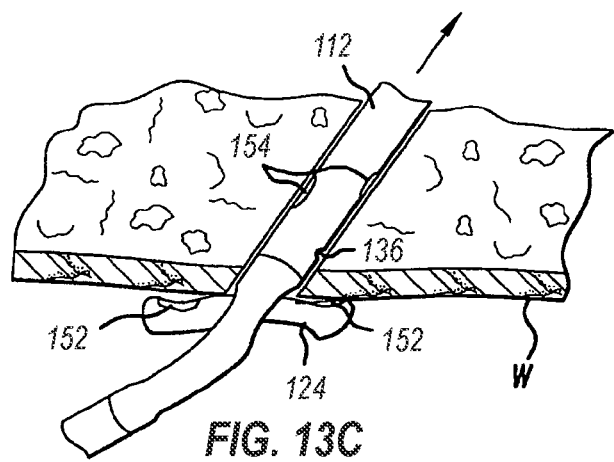

Deployment of the foot is effected by actuation of the foot deployment handle 126. Guidebody 122 helps to align the probe with the axis of the vessel V. Guidebody 122 may be set at an angle and/or offset relative to shaft 112 as appropriate to aid in alignment with a particular vessel access technique. As shown in FIG. 13C, the deployed foot 124 extends laterally from the shaft, so that foot 124 and adjacent receptacles 152 can be drawn up against vessel wall W by gently pulling shaft 112. Hence, the foot helps to accurately position the needle guides 154 at a distance from the vessel wall.

Figure 13D:
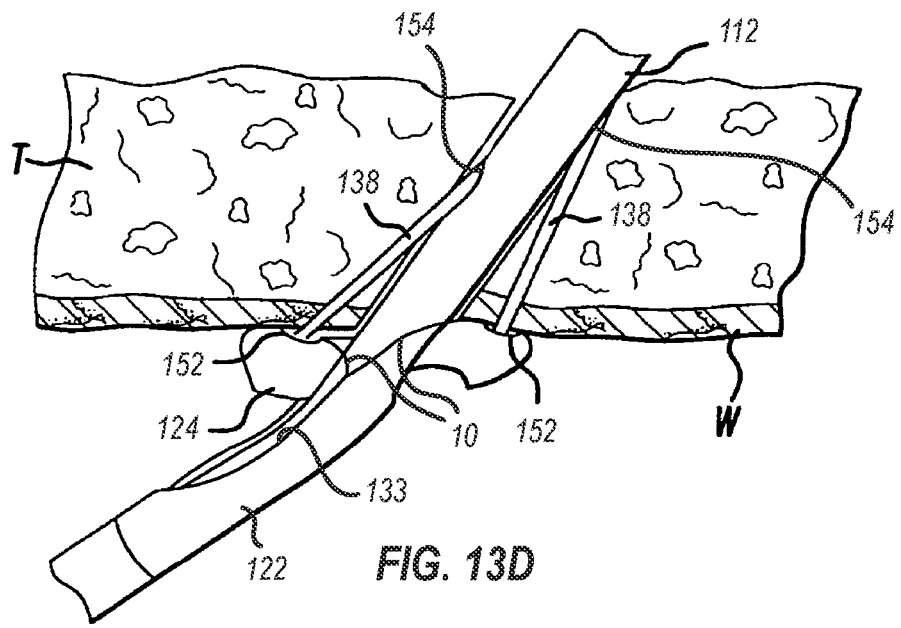

Referring now to FIG. 13D, flexible needles 138 are deflected laterally by needle guides 154 toward receptacles 152 of the deployed foot. As a result, the needles advance in cantilever both distally and laterally when needle actuation handle 120 is pressed (see FIG. 7C), and the tapering surfaces of receptacles 152 help to push the needles back into alignment with the fittings so as to overcome any unintended deflection of the needles by tissue T or vessel wall W. This ensures that needles 138 securingly engage fittings 140 within receptacles 152, thereby coupling the ends of suture 10 to the needles. While suture 10 is here illustrated running along the side of shaft 112 outside foot receptacle 130 to a lumen 133 within guidebody 122, it should be understood that the suture loop might instead extend proximally in a lumen of shaft 112, might be routed through the foot and/or foot receptacle, and/or might be stored in a spool adjacent foot 124. Regardless, suture 10 should be able to pull free of the probe between its ends to form a continuous loop across puncture P. For example, lumen 133 should be sized to allow suture 10, including knots 14, to easily slide out of lumen 133 when tension is applied to opposite ends of suture 10 through fittings 140.

Figure 13E:
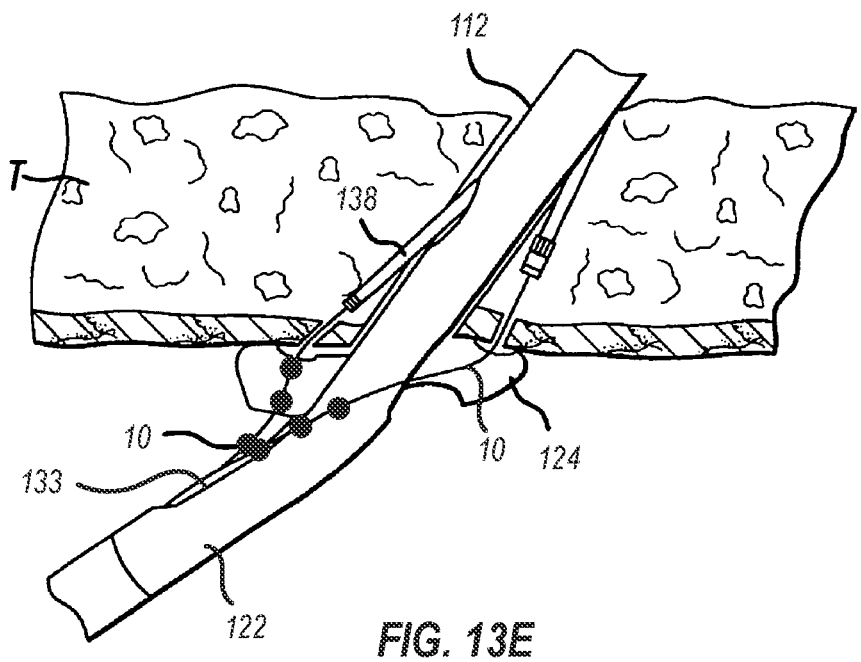
Figure 13F:
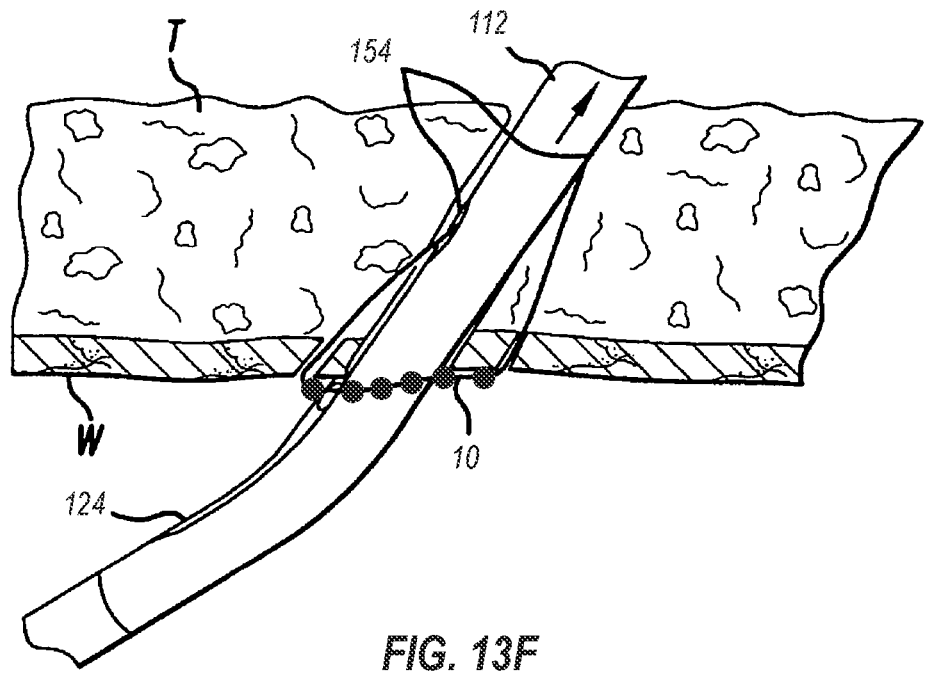

Referring now to FIGS. 13E and 13F, fittings 140 and the ends of suture 10 are drawn proximally through the vessel wall W along the needle paths formed by needles 138. Optionally, the needles may be withdrawn proximally out of the tissue tract and clear of shaft 112, or they may remain coupled to the shaft within needle guides 154. The foot actuator is moved to store foot 124 along shaft 112, and the shaft can then be pulled proximally from the tissue tract. Guidebody 122, which may comprise a soft, compliant polymer, may temporarily extend at least partially into tissue tract TT and through puncture P to help reduce the loss of blood until the loop is secured.

Figure 13G:
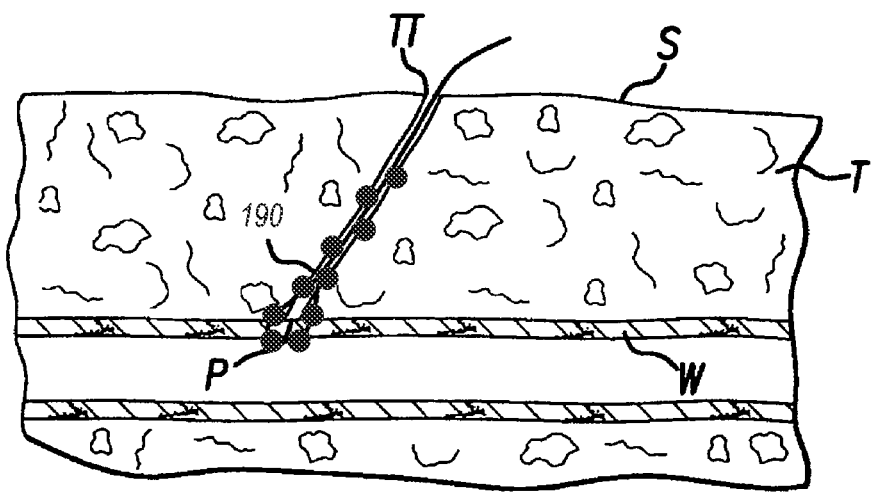

Now referring to FIG. 13G, once shaft 112 has been withdrawn sufficiently to expose needle guides 154, the ends of the suture loop can be grasped by the operator. The operator may then continue to apply tension on opposite ends of suture 10 until the tissue adjacent the puncture is drawn closed and knots or anchors 14 are positioned to retain the tissue in a closed or sealed position. As mentioned above, the operator still has the option to manually tie a knot in the suture limbs to further secure the closure.

An alternative vessel closure probe 170, which is adapted for positioning and deploying the second embodiment of the self-locking/securing suture shown in FIGS. 3 and 4, will be explained with reference to FIGS. 14A to 14E. This embodiment includes an articulatable foot 124 having a pair of needle receptacles 152, as described above. Although each needle receptacle 152 contains a fitting 140 for coupling a flexible filament to a tip of an associated needle, the filament in this case comprises a short length of suture 174 (or some temporary connecting filament, as shown schematically in phantom in FIG. 14A) spanning directly between the needle receptacles. Rather than pulling the two ends of an extended loop through the needle paths and proximally out the tissue tract for tying, closure system 170 advances a single end of the suture distally along one needle path, across the puncture, and then proximally along the other needle path. To provide this interaction, at least one needle includes means for attaching suture 10 to short suture 174, here in the form of a detachable coupling structure carried on the at least one needle.

Figure 14A:
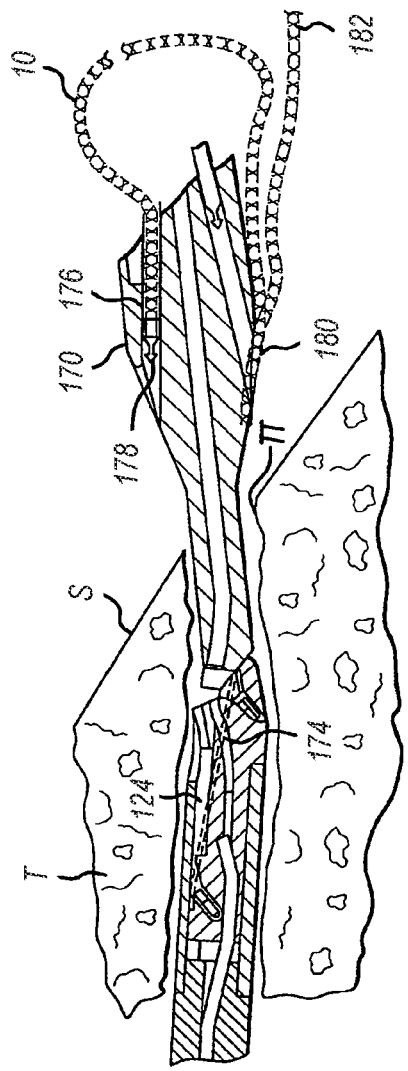
FIGS. 14A-14E illustrate another embodiment of a self-locking suture mediated closure system and method adapted for use with the self-locking/securing suture embodiment shown in FIG. 3.
Figure 14B:
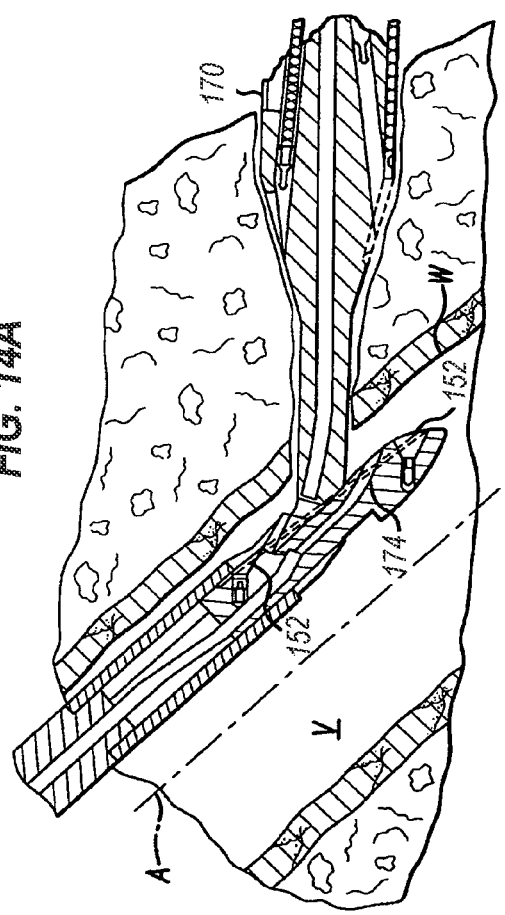

Referring now to FIGS. 14A and 14B, the distal end of probe 170 advances distally through skin S and into a tissue T of the patient while the probe is in the small profile configuration with foot 124 aligned along the axis of the probe. Here, however, an end 176 of suture 10 is affixed to a detachable needle tip 178 of a hollow needle 138'. Detachable tip 178 comprises a fitting having an opening receiving an end of suture similar to fitting 140, attached to a barbed needle end (similar to that of needle 138). Suture 10 may extend proximally within hollow needle 138 where the needle has an open channel along its length, may exit the hollow needle just proximally of detachable tip 178, or may be disposed alongside a solid needle. Needle 138 (opposite hollow needle 138') has a fixed barbed tip, as described above. A second end 182 of suture 10 extends proximally along the shaft of the probe, the second end of the suture optionally also being releasably held along the shaft.

Probe 170 advances along tissue tract TT to puncture P in blood vessel V. Once foot 124 is disposed within a blood vessel V, a pull wire moves the foot proximally and pivots the foot laterally so that the foot extends along an axis A of the vessel, as illustrated in FIG. 14B. The foot can then be pulled proximally against an inner surface of the vessel wall W to ensure that the needle receptacles 152 are properly positioned.

Figure 14C:
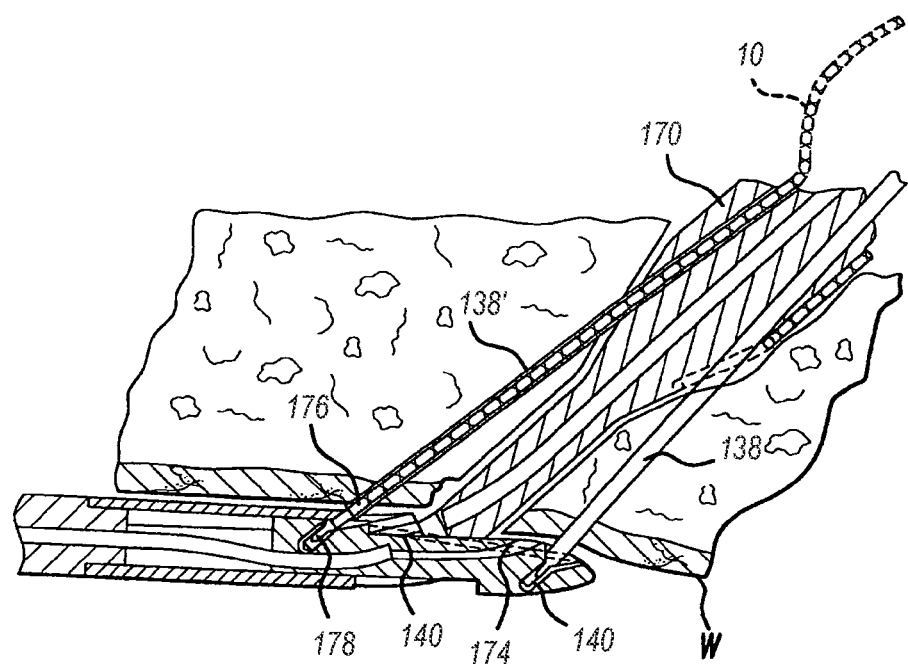
Figure 14D:
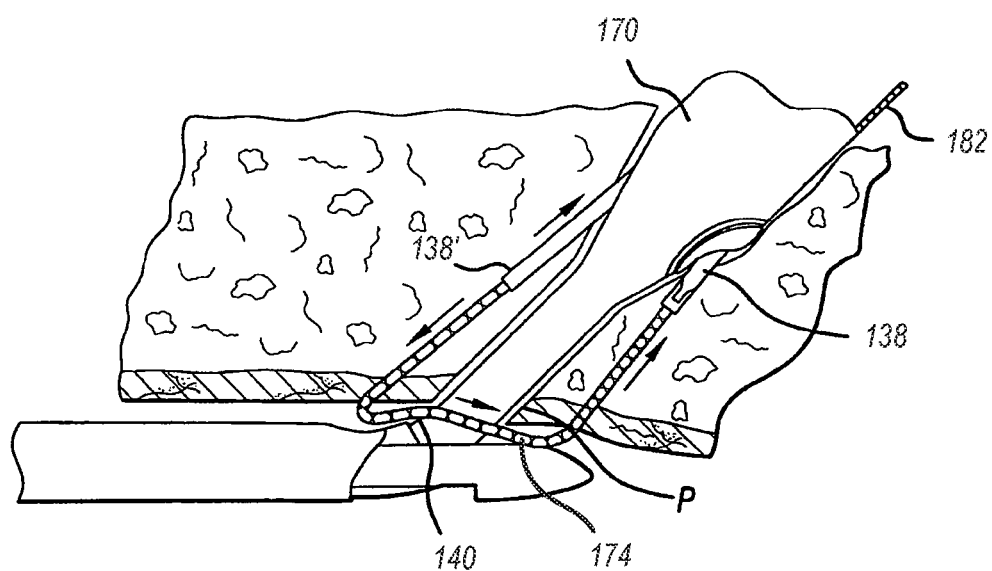

As can be understood with reference to FIGS. 14C and 14D, hollow needle 138' and needle 138 advance to engage fittings 140 within receptacles 152. Hollow needle 138' draws the first end 176 of suture 10 distally through vessel wall W, and detachable tip 178 is secured into an associated fitting 140 using the barb and tab interaction described above. As short suture 174 extends between fittings 140, and as detachable tip 178 can pull free of hollow needle 138' when the needles are withdrawn, this effectively couples needle 138 to first end 176 of suture 10. The detachable tip riding partially within the hollow needle (or vice versa) so that the assembly remains together under compression. Hence, needle 138 can pull the suture distally along the needle path formed by hollow needle 138', across the puncture P, and proximally along the needle path formed by needle 138, as illustrated in FIG. 14D. Probe 170 may also include a bearing surface (not shown), positioned within the vessel lumen and around which short suture 174 and/or suture 10 may travel, to assist in guiding and/or supporting short suture 174 and/or suture 10 as it passes through a portion of vessel lumen.

Figure 14E:
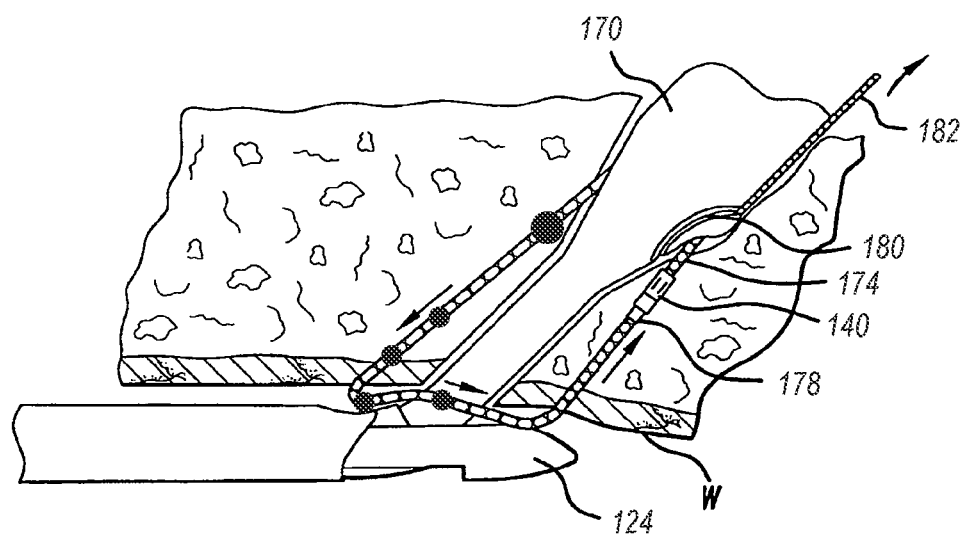

Once the suture has been drawn through the tissue adjacent the access puncture and the suture limbs are drawn proximally through the tissue tract and exposed to the operating outside the surface of the skin, then the closure device can be removed. With the closure device, the operator can then pull the end of one of the suture limbs to draw the knots or anchors through the tissue to securely close and seal the puncture, as Illustrated in FIG. 14E and as previously described above in relation to FIGS. 3 and 4.

While the foregoing examples have focused on closing a vascular access opening, the inventive concept disclosed herein can also be adapted to close other types of openings (i.e., punctures, incisions, structural defects, etc.) in tissue. In one embodiment, a suture with a plurality of knots or anchors formed in the bight as described above can be positioned on one side of the opening, from the other side of the opening a pair of needles can be advanced through tissue adjacent the opening and capture opposing ends of the suture limbs, respectively, and then the needles can be withdrawn, thereby drawing successive knots or anchors through the tissue until the opening is closed and held in place by two or more of the knots or anchors. In another embodiment, the suture and the needles can initially be deployed on the same side of the opening, with the needles being capable of drawing one end of the suture first in a first direction through tissue located to one side of the opening and then drawing that same end of the suture in a substantially opposite direction through tissue located on the other side of the opening thereby drawing successive knots or anchors through the tissue until the opening is closed and held in place by two or more of the knots or anchors.

While the exemplary embodiments have been described in some detail for clarity of understanding, a wide variety of modifications, adaptations, and changes will be obvious to those of skill in the art. For example, some of the benefits of the present invention might be provided by actuating a foot disposed outside the blood vessel within the tissue tract, and advancing needles from within the blood vessel proximally through the vessel wall toward the actuated foot. Hence, the scope of the present invention is limited solely by the appended claims.

What is claimed is:

1. A system for closing an opening in a vessel wall, wherein a tissue tract provides access to the opening for performing medical procedures, the system comprising:
   a housing with a shaft extending from the housing;
   an actuation handle operatively coupled to the proximal housing and configured to deploy a foot disposed distal the housing;
   a needle actuation handle operatively coupled to a first needle to and configured deploy the first needle to penetrate the vessel wall and cooperate with the foot;
   a suture comprising a first fitting and a plurality of pre-tied anchors, spaced apart along a length of the suture and between the first end to the second end of the suture, the first fitting being configured to cooperate with the first needle, wherein, upon
   proximal movement of the first needle cooperating with the first fitting and deployed in tissue, the suture is configured to pull opposing edges of the vessel wall together and pull opposing edges of the tissue together to engage the plurality of pre-tied anchors against a distal surface of the tissue within the tissue tract and against a proximal surface of the vessel wall on anterior and posterior sides of the opening with a plurality of the plurality of the pre-tied anchors being disposed within the tissue tract and extending proximally towards a proximal end of the tissue tract, and
   the engagement of the plurality of pre-tied anchors with the tissue and the vessel wall prevent pulling of the second end of the suture through the vessel wall without tails of the suture being tied in a knot.

2. The system of claim 1, wherein each of the plurality of pre-tied anchors is configured frictionally engage the tissue, such that a combined force of friction proved by the plurality of pre-tied anchors is about 2 Newtons to about 6 Newtons.

3. The system of claim 1, wherein the plurality of pre-tied anchors are symmetrically spaced on the suture.

4. The system of claim 1, wherein a plurality of the plurality of pre-tied anchors are spaced between about 0.020" and about 0.039" apart.

5. The system of claim 1, wherein the plurality of pre-tied anchors comprises a first group of pre-tied anchors and a second group of pre-tied anchors, the first group and the second group being separated by a distance greater than a distance between adjacent pre-tied anchors within each of the first group and the second group.

6. The system of claim 1, wherein the suture comprises a pre-formed tissue engaging structure that resist movement of the suture.

7. The system of claim 6, wherein the pre-formed tissue engaging structure comprises a heat-formed structure.

8. The system of claim 6, wherein the pre-formed tissue engaging structure comprises a plurality of randomly formed peaks and troughs.

9. The system of claim 6, wherein the pre-formed tissue engaging structure comprises a plurality of systematically formed peaks and troughs.

10. The system of claim 1, wherein each pre-tied anchor has a diameter of about 0.011" to about 0.036".

11. The system of claim 1, wherein the pre-tied end anchor has a diameter of about 0.038" to about 0.052".

12. The system of claim 1, wherein a tissue engaging surface area formed by the plurality of pre-tied intermediate anchors is about 0.1" to about 0.6".

13. A system for closing an opening in a vessel wall, wherein a tissue tract provides access to the opening for performing medical procedures, the system comprising:
   a housing with a shaft extending from the housing;
   an actuation handle operatively coupled to the proximal housing and configured to deploy a foot disposed distal the housing;
   a needle actuation handle operatively coupled to a first needle and configured to deploy the first needle to penetrate the vessel wall and cooperate with the foot;
   a suture comprising a first fitting, a pre-tied end-anchor at a first end, a plurality of pre-tied intermediate anchors spaced apart along a length of the suture from the first end to the second end, the suture further comprising shape-memory structures along the length of the suture which resist movement of the suture, the first fitting being configured to cooperate with the first needle, wherein, upon actuation of the needle actuation handle and
   proximal movement of the first needle deployed in tissue, the suture is configured to pull opposing edges of the vessel wall together, pull opposing edges of the tissue together to engage the pre-tied end-anchor, the plurality of pre-tied intermediate anchors against a distal surface of the tissue within the tissue tract and against a proximal surface of the vessel wall on anterior and posterior sides of the opening, and partially uncoil the shape-memory structures, and
   wherein the plurality of pre-tied anchors and the shape-memory structures are configured to engage with the tissue and the vessel wall and prevent pulling of the second end of the suture through the vessel wall without tails of the suture being tied in a knot.

14. The system of claim 13, wherein each of the plurality of pre-tied intermediate anchors is configured to frictionally engage the tissue, such that a combined force of friction proved by the plurality of pre-tied intermediate anchors is about 2 Newtons to about 6 Newtons.

15. The system of claim 13, wherein the plurality of pre-tied intermediate anchors are symmetrically spaced on the suture.

16. The system of claim 13, wherein a plurality of the plurality of pre-tied intermediate anchors are spaced between about 0.020" and about 0.039" apart.

17. The system of claim 13, wherein the pre-formed tissue engaging structure comprises a plurality of formed peaks and troughs.

18. The system of claim 13, wherein each pre-tied intermediate anchor has a diameter of about 0.011" to about 0.036".

19. The system of claim 13, wherein the pre-tied end anchor has a diameter of about 0.038" to about 0.052".

20. The system of claim 13, wherein a tissue engaging surface area formed by the plurality of pre-tied intermediate anchors is about 0.1" to about 0.6".

* * * * *